United States Patent
Symonds et al.

(10) Patent No.: US 9,164,111 B2
(45) Date of Patent: Oct. 20, 2015

(54) DEVICE FOR MULTIPLE TESTS FROM A SINGLE SAMPLE

(75) Inventors: John W. Symonds, Huntsville, AL (US); Mark Wells, Athens, AL (US)

(73) Assignee: Resolved Technologies, Inc., Toney, AL (US)

( * ) Notice: Subject to any disclaimer, the term of this patent is extended or adjusted under 35 U.S.C. 154(b) by 0 days.

(21) Appl. No.: 12/046,792

(22) Filed: Mar. 12, 2008

(65) Prior Publication Data
US 2008/0225295 A1 Sep. 18, 2008

Related U.S. Application Data

(60) Provisional application No. 60/906,369, filed on Mar. 12, 2007.

(51) Int. Cl.
| | |
|---|---|
| *G01N 1/10* | (2006.01) |
| *B01D 15/08* | (2006.01) |
| *G01N 15/06* | (2006.01) |
| *G01N 35/00* | (2006.01) |
| *G01N 21/25* | (2006.01) |
| *G01N 1/18* | (2006.01) |
| *G01N 21/07* | (2006.01) |
| *G01N 1/20* | (2006.01) |
| *G01N 21/11* | (2006.01) |
| *G01N 27/04* | (2006.01) |
| *G01N 27/28* | (2006.01) |
| *G01N 21/03* | (2006.01) |

(52) U.S. Cl.
CPC ........ *G01N 35/00069* (2013.01); *G01N 21/253* (2013.01); *G01N 1/18* (2013.01); *G01N 1/2035* (2013.01); *G01N 21/07* (2013.01); *G01N 21/11* (2013.01); *G01N 27/04* (2013.01); *G01N 27/28* (2013.01); *G01N 2021/0328* (2013.01)

(58) Field of Classification Search
CPC ............ G01N 35/00069; G01N 21/07; G01N 2021/0325; G01N 1/2035; G01N 1/18
USPC ........................................ 356/246; 73/863.61
See application file for complete search history.

(56) References Cited

U.S. PATENT DOCUMENTS

| | | | | |
|---|---|---|---|---|
| 3,688,216 | A * | 8/1972 | Kocher et al. | 372/54 |
| RE28,800 | E * | 5/1976 | Acker et al. | 356/201 |
| 4,244,916 | A * | 1/1981 | Guigan | 422/72 |
| 4,288,206 | A | 9/1981 | Tigwell et al. | |
| 4,538,683 | A | 9/1985 | Chulick | |
| 4,576,054 | A | 3/1986 | Lalin | |
| 4,940,332 | A * | 7/1990 | Miwa et al. | 356/417 |
| 5,061,381 | A * | 10/1991 | Burd | 210/789 |
| 5,391,352 | A * | 2/1995 | Hendrix et al. | 422/65 |
| 5,472,603 | A * | 12/1995 | Schembri | 210/380.1 |

(Continued)

*Primary Examiner* — Michael A Lyons
*Assistant Examiner* — Rebecca C Bryant
(74) *Attorney, Agent, or Firm* — Maynard Cooper & Gale, P.C.; Jon E. Holland

(57) ABSTRACT

A sample device and method for analyzing a sample are claimed. The sample device is a flat disc containing channels and wells for directing a sample to reagents located in the disc and for mixing the sample with the reagents. The disc is mounted on an analyzer and the sample is pumped into the disc, divided into a plurality of sub-sample, and at least some of the sub-samples are mixed with a number of reagents. The resultant analytes are analyzed spectrophotometrically for a determination of the concentration of various substances in the sample. The present invention permits multiple tests to be performed quickly and automatically with minimal operator involvement.

33 Claims, 3 Drawing Sheets

(56) References Cited

U.S. PATENT DOCUMENTS

| | | |
|---|---|---|
| 5,553,508 A | 9/1996 | Dabberdt et al. |
| 5,591,643 A * | 1/1997 | Schembri ............... 436/45 |
| 5,686,673 A | 11/1997 | Kabis |
| 5,717,147 A | 2/1998 | Basch et al. |
| 5,726,360 A | 3/1998 | Keefer |
| 6,030,581 A * | 2/2000 | Virtanen ............... 422/68.1 |
| 6,097,831 A * | 8/2000 | Wieck et al. ............ 382/128 |
| 6,268,219 B1 * | 7/2001 | Mcbride et al. ........... 436/180 |
| 6,520,313 B1 * | 2/2003 | Kaarakainen et al. ..... 198/369.5 |
| 6,762,842 B2 | 7/2004 | Pfeifer et al. |
| 6,872,545 B2 * | 3/2005 | Griner et al. ............ 435/33 |
| 7,604,778 B2 * | 10/2009 | Dause ............... 422/102 |
| 2004/0020834 A1 * | 2/2004 | Mincsovics et al. ....... 210/198.2 |
| 2004/0137640 A1 * | 7/2004 | Hirao et al. ............ 436/514 |
| 2006/0091085 A1 * | 5/2006 | Kobayashi et al. ......... 210/787 |

\* cited by examiner

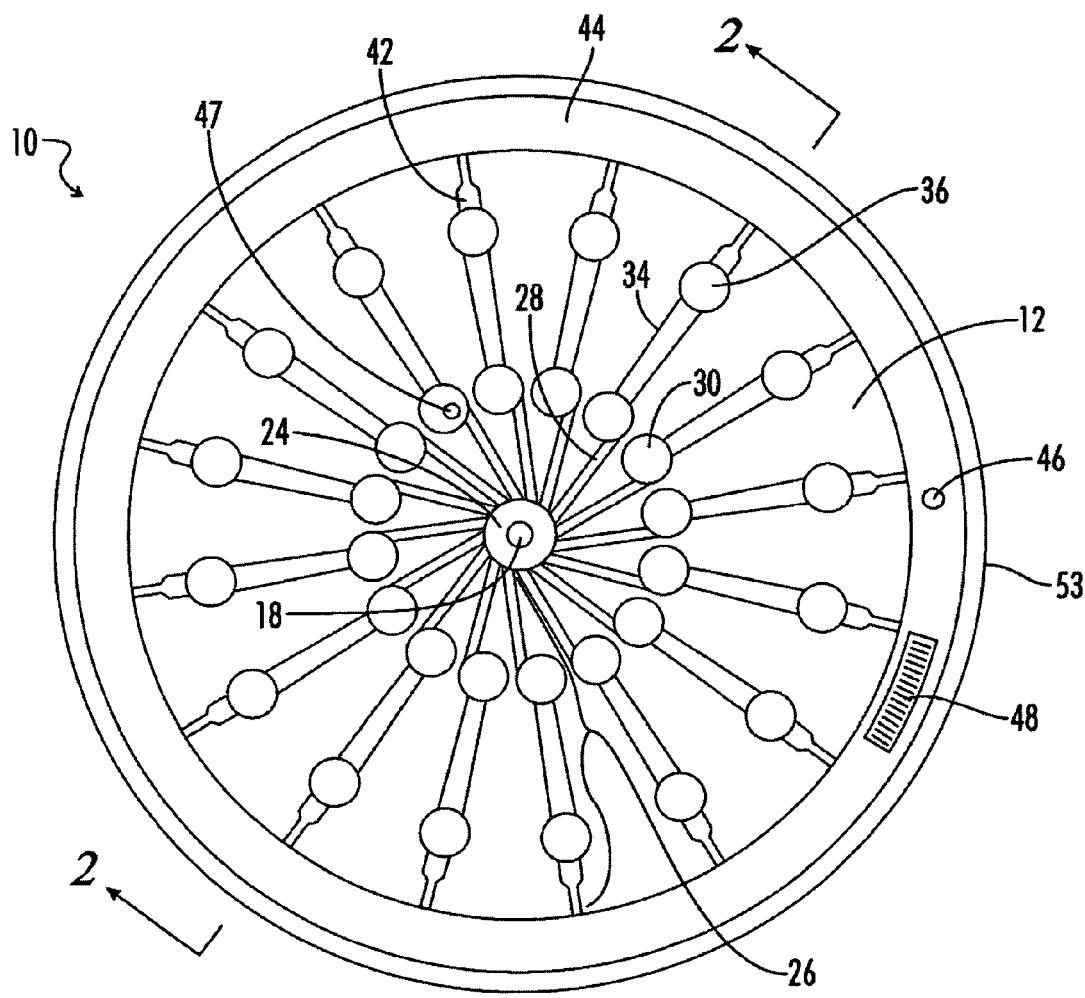
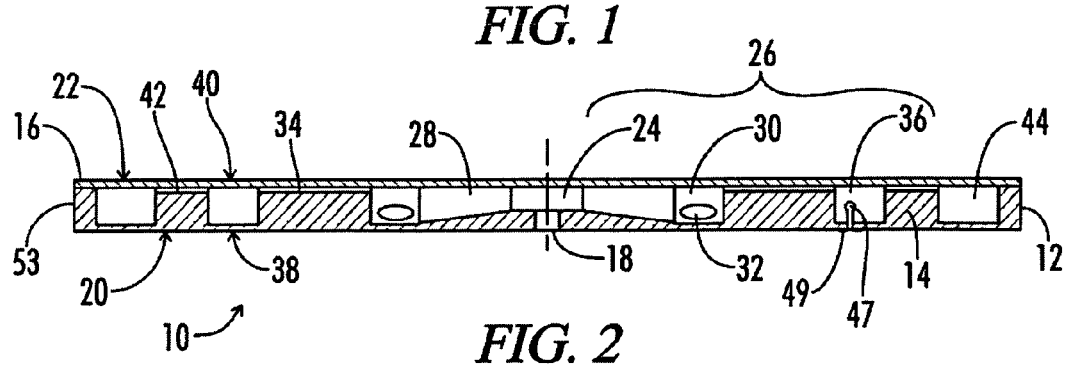
FIG. 1
FIG. 2

DEVICE FOR MULTIPLE TESTS FROM A SINGLE SAMPLE

This application claims the benefit of U.S. Provisional Application No. 60/906,369, filed Mar. 12, 2007.

BACKGROUND OF THE INVENTION a. Field of the Invention

The present invention relates generally to the field of chemical testing of a sample. More particularly, the invention provides a system and method for rapid testing of water quality via a small device that permits multiple tests to be performed simultaneously and automatically from a single sample.

b. Description of the Related Art

The process of preparing water for consumption in this country is highly regulated—nationally by the Environmental Protection Agency, and locally by state environmental agencies. Although the water treatment process is fairly straightforward, documenting that all proper precautions have been taken to protect the consumer can be a tedious and time-consuming process. In many other countries, resources are not as readily available to test water quality and, unfortunately, water is distributed for consumption containing many dangerous mineral and biological contaminants. The present invention is intended to simplify and expedite the analytical aspect of water treatment.

Overview of the Water Process

Utilities may obtain water from rain water runoff collected in rivers, lakes, and streams, or from wells. Fresh, untreated water is referred to as "raw" water. The raw water is pumped to a water treatment plant, where analytical tests are performed to determine the quality of the raw water. The water is then filtered to remove debris and other turbid materials, and chemicals are added to improve the quality of the water. The water is then referred to as "finished" water. The finished water must be tested and held to regulated standards before being released to the distribution system. If the finished water passes all tests, it is pumped to water tanks where it is held in waiting for the consumer.

Almost all water systems currently employ at least one operator who is responsible for laboratory procedures. Small labs are kept in-house in order to maintain the water system in compliance with certain mandatory tests that must be performed frequently. In fact, many tests are required to be performed every hour, a laborious and time-consuming undertaking.

The water quality tests generally consist of a spectrophotometric analysis on 10-25 milliliter water samples of both raw and finished water. The water samples are mixed with chemical reagents and analyzed at a reagent-specific wavelength in order to determine the concentration of certain components in the water samples. Most analytes requires their own specific reagent and each test must be run independently from the other tests. For tests that are required frequently, this requires a series of analyses to be performed hourly.

Although this manual method of testing is the standard across the industry, it is not without problems. The series of tests that must be performed is slow and tedious. Operators spend, on average, approximately twenty minutes of each hour performing simple analyses, and often more complex tests are left undone just because there is not enough time or man-power to do them. In some cases, multiple analytical devices must be purchased to increase the testing capacity of the water system.

Sample size is an issue as well, not in that a water plant cannot spare a few milliliters of water to run these tests, but because the actual sample being analyzed is not truly indicative of the entire water sample. A spectrophotometer works by shooting a beam of electromagnetic radiation at a particular wavelength through a sample and measuring the amount of electromagnetic radiation absorbed by the sample. One form of electromagnetic radiation is light, as from a light bulb. This beam of electromagnetic is, at most, 10 millimeters in diameter. When considering the size of a 25 milliliter sample vial, the test actually sees less than 10% of the total sample volume. If the sample is not 100% homogenous, the test results can be inaccurate. By the reagent manufacturer's own standards, a 100% homogenous mixture may not be achieved on most reagent-sample mixtures unless constantly stirred for more than one hour, which is not practical in this situation. Other tests which involve shooting a beam of electromagnetic radiation at a particular wavelength through a sample and measuring the amount of electromagnetic radiation coming from the sample are also possible, such as fluorescence testing.

Also, repetitive testing by humans is inefficient. Tedious analytical tests such as these lead to increased user error and careless mistakes. Many test operators are not trained as laboratory technicians, but are expected to perform as such and are held responsible for laboratory practices.

Unfortunately, the water treatment industry has been undeserved in the development of new technology to remedy these problems. Prior art devices have been designed to perform automated water quality testing, but the prior art devices require sophisticated manufacturing techniques. It would be desirable to have a system and method for rapid and repetitive testing of water quality that permits simple and economical testing of water samples.

SUMMARY OF THE INVENTION

The current invention is a sample device where one sample is injected or input into the device one time, and a plurality of different chemical analyses are independently performed on the sample to provide several different test results. The sample is split into a plurality of different sub-samples, where each sub-sample is directed through a channel to an optical well. Electromagnetic radiation is transmitted through the optical well, and a detector detects how much electromagnetic radiation leaves the optical well. Light is frequently the preferred type of electromagnetic radiation used, and the amount of electromagnetic radiation leaving the optical well indicates the amount of a substance present in the sample. Before the sub-sample flows into the optical well, it can be directed through a reagent well containing a reagent specific to the chemical test to be performed. The reagent is then dissolved, and can react with specific compounds which may be in the sub-sample. The use of a specific reagent is required for many of the tests performed, and the reagent well and the channel between the reagent and optical well aid in dissolving the reagent in the sample.

An analyzer is used in conjunction with the sample device to perform the chemical tests. The sample device is aligned on the analyzer, and different sources of electromagnetic radiation are transmitted through the different optical wells. The analyzer can be designed with fewer radiation sources than optical wells in the sample device, so the sample device can be automatically rotated so the radiation source is transmitted through a second optical well after the first test is completed. This rotation and subsequent testing can be repeated as often as desired, so if the sample device had 16 optical wells, and the analyzer had 4 radiation sources, there could be 4 consecutive tests performed.

In one embodiment, the sample device according to the present invention will allow users to monitor the quality of a water sample more quickly and more effectively than with conventional methods. Current testing is very time consuming, inefficient, and expensive. The sample device method will allow multiple tests to be run simultaneously and data to be automatically logged. Sample volumes will also be much reduced and the training needs for laboratory personnel will be simplified. The water system operator will simply have to load the water sample onto the disc and place it in the analytical device. The unit can be designed to automatically pump the water sample across several reagents simultaneously, take spectrophotometric readings, and generate a report showing the findings of each individual test.

One objective of the present invention to provide a low cost, disposable device and analysis system to enable rapid and automatic water quality testing.

Another objective of the present invention to provide for automatic uploading of water quality testing data.

It is a further objective of the present invention to improve the mixing of the water sample with reagents for a more homogenized mixture when the sample is mixed.

Another objective is to provide a simple to operate system for routine chemical analysis.

Yet another objective is to improve lab safety by minimizing the number of operations and the amount and exposure to reagents for the laboratory technician.

These and other objectives will be achieved by the device described in more detail in the detailed description.

DESCRIPTION OF THE DRAWINGS

FIG. 1 is a top view of the sample device according to one embodiment of the present invention.

FIG. 2 is a cross-sectional representation of the sample device illustrated in FIG. 1, taken approximately along lines 2-2.

DETAILED DESCRIPTION

Figure 3:
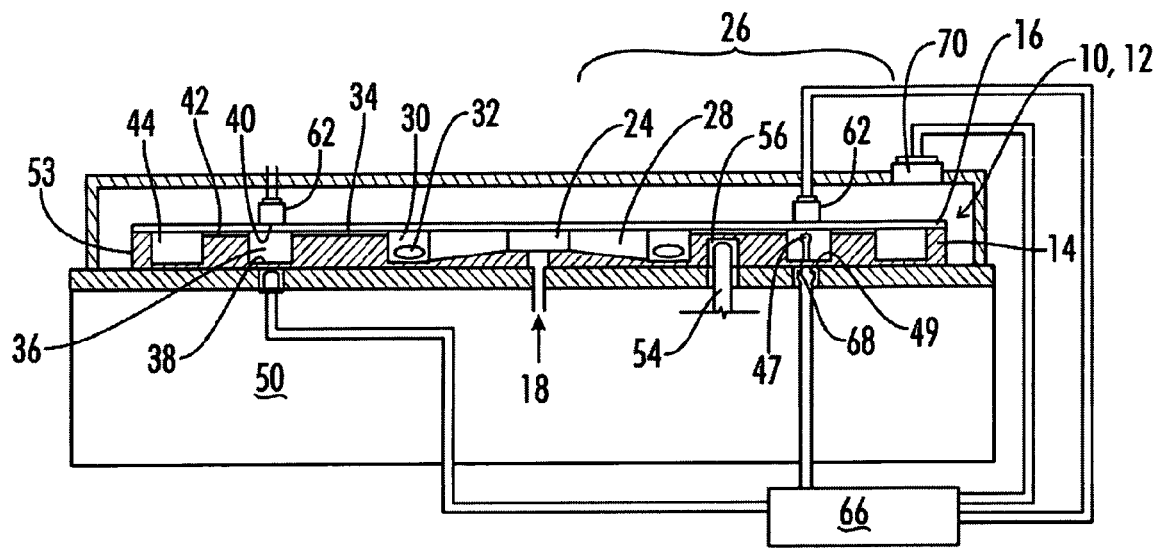
FIG. 3 is a cross-sectional representation of the sample device mounted on the analyzer according to one embodiment of the present invention.

The present invention can be used for a wide variety of sample testing applications, and this disclosure is not intended to limit the invention to any one particular embodiment. One potential use of the current invention is for the routine testing associated with water treatment facilities, and the current discussion is geared for this particular application. However, other possible uses also exist, and this discussion is not intended to limit the invention to this application. Those skilled in the art will recognize there are other uses and/or applications of the current invention which are intended to be included in this description.

Sample Testing Background

The principles and method of operation of the water quality analysis performed by the present invention are well known to persons of skill in the art. The method works on principles of light absorption; specifically, when an electromagnetic radiation beam crosses a substance, some of the radiation is absorbed by atoms, molecules or crystal lattices in the substance. Specific chemical compounds absorb specific wavelengths of electromagnetic radiation, so the concentration of these specific compounds can be determined by measuring how much electromagnetic radiation of a chosen specific wavelength is absorbed. Light is one form of electromagnetic radiation, and is the radiation source referenced in this discussion. Spectrophotometric chemical analysis can be based on the creation of an absorbing compound from a specific chemical reaction between a sample and a specific reagent. Beer's law states that when an absorbing compound absorbs light of a particular wavelength, the absorbance is directly proportional to the concentration of the absorbing compound in solution, as long as other factors are constant. The current system generally keeps the other factors constant, so the absorbance is proportional to the concentration of the absorbing compound.

The analysis of the sample is accomplished by first mixing the sample with a reagent and then placing the mixed sample in between a light source and a detector which can measure the amount of light striking the detector. The amount of light passing through the sample (i.e., the radiation that is not absorbed by the sample) is detected by a detector or photometer which converts the light energy into a voltage signal. The photometer sends the voltage signal through an amplifier to a microprocessor which then correlates the voltage signal with the concentration of the absorbing atoms and molecules based upon the wavelengths which are absorbed and the amount of light which is absorbed.

While the principles are well known in the art, the present invention enables the user to perform multiple tests simultaneously by providing a disposable sample device pre-loaded with multiple reagents. For example, if the sample device includes 16 different test sites, the following tests can be performed from a single sample injected into a single sample device. These tests are commonly required for water treatment facilities.

| | |
|---|---|
| Total Iron | $CaCO_3$ Content (Hardness) |
| Ferrous Iron | Carbon Dioxide Content |
| Manganese | Sodium |
| Calcium | Total Sulfates |
| Magnesium | Aluminum |
| Fluoride | Silver |
| Total Chlorine | Color |
| Free Chlorine | Turbidity |

The sample device can be configured to support different types of water sample tests that may be needed for different water utilities. For example, a city using well water may need to perform different tests than a city using river water. The reagents in the sample device can be customized to support the type of water utility that will be using the sample device. The sample device can also be configured to support sampling applications other than testing water for utilities.

Other tests which are more common in other industries include fluorescence testing and electrochemical testing. In fluorescence testing, one wavelength of electromagnetic radiation, often in the ultraviolet frequency, is transmitted into the sample, which absorbs energy from the radiation source. The sample material then re-transmits a longer wavelength of electromagnetic radiation, and the amount of the longer wavelength transmitted depends on the concentration of a particular molecule in the sample.

In electrochemical testing, a probe is inserted into the sample, and the voltage, current, and/or resistance transmitted by the probe can be equated to a specific characteristic of the sample. For example, with a pH probe, the voltage potential between the probe and the hydrogen ions in the sample solution is measured, and in a conductivity probe, the electrical resistance of the sample solution is measured.

Sample Device

The present invention and its advantages are best understood by referring to the drawings. The elements of the drawings are not necessarily to scale, emphasis instead being placed upon clearly illustrating the principles of the invention.

One embodiment of the present invention includes a sample device 10 for preparing fluid samples as shown in FIGS. 1 and 2. Reference to fluid samples is intended to include samples which are fluids as well as samples typically considered to be solids, but which are able to flow, such as sand. The sample device 10 is in the shape of a disc with wells for introducing the sample to various reagents, channels for mixing the sample with the reagents and directing the sample flow, and wells for analyzing the sample. The sample device 10 is also referred to as the disc 10 in this description.

In this embodiment, the disc 10 is relatively thin and is fabricated from a transparent material such as a plastic material. The disc can also be fabricated from glass, quartz, or even photopolymers used in stereo lithography such as polydimethylsiloxane (PDMS.) The disc 10 has a body 12, including a bottom plate 14 and a lid 16. The lid 16 is generally a solid flat disc enclosing the top of the body 12. The lid 16 is permanently affixed to the disc 10 by sonic welding, adhesive or other means such that a seal is formed between the lid 16 and the bottom plate 14. A full surface bond between the lid 16 and the bottom plate 14 is desired. In one embodiment of the invention, the lid 16 is 1/16 inches thick, though other thicknesses are possible without departing from the scope of the invention. Generally, the cavities and paths defined in the body 12 are formed in the body bottom plate 14, and the lid 16 is used to enclose and seal these paths and cavities. There can be a base (not shown) affixed to the bottom of the body bottom plate 14, either in place of the lid 16 or in addition to the lid 16.

The disc 10 has in its center an inlet port 18 in the form of a cylindrical through hole. Preferably, there is only one inlet port 18 per disc 10. This inlet port 18 is defined in the body 12, and passes into the body bottom plate 14. In this embodiment, the sample enters the disc 10 through the inlet port 18 from a disc bottom surface 20, though in other embodiments the sample is introduced from a disc top surface 22. The inlet port 18 provides access and fluid communication from outside of the disc 10 to an inlet well 24 defined in the disc body 12. Once the sample is introduced to the inlet well 24, it is divided into sub-samples. The inlet well 24 can be concentric with the inlet port 18, and is usually larger in diameter than the inlet port 18. In one embodiment of the present invention, the inlet well 24 is 1/4 inches deep, though other dimensions are possible within the scope of the invention.

There are several features defined within the disc body 12 below the top surface 22, and these features serve to contain, direct and mix the sample during the sample testing process. A plurality of channels 26 radiate from the inlet well 24. The channels 26 include various channel sections, including a plurality of reagent channels 28 which connects the inlet well 24 to a plurality of reagent wells 30. The reagent channels 28 provide fluid communication between the inlet port 18 and the reagent wells 30. The reagent wells 30 can be generally cylindrically shaped, and are dimensioned with a sufficient depth to contain a reagent 32. A plurality of reagents 32 can be pre-loaded into the reagent wells 30. As is known by persons of skill in the art, some reagents 32 are in solid tablet form. Other reagents 32 are typically in liquid form, and may be loaded in the disc 10 in a semi-solid (e.g., "gel-cap") form.

For several tests, the reagents 32 need to be mixed and dissolved in the sample before the sample is tested. Typically the reagents 32 react with a particular component which may be in the sample, and the compound resulting from the reaction absorbs the light and is detected by the testing procedure. Therefore, the reagent should be thoroughly mixed with the sample for the most accurate test results. The reagent channel 28 can enter the reagent well 30 at close to a tangent of the reagent well 30 to help facilitate swirling and mixing within the reagent well. The dimensioning of the reagent well 30 and reagent channel 28 to facilitate swirling and agitation utilizes the fluid flow to aid in dissolving the reagent 32 in the sample. The reagent channels 28 can be similar in depth to the reagent well 30 to facilitate swirling and mixing in the reagent well 30 as the sample material enters.

The channels 26 also include optical channels 34 which connect and provide fluid communication between the reagent wells 30 with a plurality of optical wells 36. Preferably, the optical channels 34 are shallow, and serve as mixing channels to further mix the reagent 32 and the sample before the sample is spectrophotometrically tested. The optical channels 34 are dimensioned and sized so the fluid flowing through the channels 34 tends to agitate and mix the sample, and this enhances efficient mixing of the reagents 32 with the samples. The optical channels 34 can be more shallow than the optical wells 36 or the reagent wells 30 to reduce the cross sectional area of the optical channels 34 and therefore increase the Reynolds number in the optical channels 34. This tends to enhance mixing by promoting turbulent flow in the sample.

If a particular test or standard does not require a reagent 32, the inlet well 24 can be directly connected to the optical well 36 by the optical channel 34, with no reagent channel 28 or reagent well 30 between the inlet well 24 and the optical well 36. As an alternative, the disc 10 can be designed with the reagent channel 28 and reagent well 30 between the inlet well 24 and the optical well 36, but the reagent well 30 can be left empty with no reagent 32. Either way, the sample can be directed to the optical well 36 without being mixed with a reagent 32, if desired.

Optical wells 36 can be generally cylindrical wells defined in the body 12 to permit light to shine from beneath the disc 10 through the optical well 36 containing the sample to detectors received above the optical wells 36, or vice versa. Therefore, the optical well bottom surface 38 and the optical well top surface 40 should be transparent to the wavelength of light used, and the top and bottom surfaces 38, 40 should be smooth to minimize diffraction and scattering of the light signal. It is acceptable for the top and bottom surfaces 38, 40 to absorb some of the light, as long as enough light is allowed to pass for an accurate test of the sample to be performed. In one embodiment of the invention, the reagent wells 30 and optical wells 36 are 30 inches deep, though other dimensions are possible.

Waste channels 42 are sized to permit excess sample to exit the optical wells 36 and be received in an exterior waste well 44, which can follow the perimeter of the disc 10. Therefore, the waste channels 42 connect and provide fluid communication between the optical wells 36 and the waste well 44. The waste well 44 is sufficiently deep to contain excess water or sample material. The waste channels 42, which are another part of the channels 26, can narrow at their entrance to the waste well 44 in order to reduce the possibility of backflow of sample material from the waste well 44 into the waste channels 42.

The lid 16 can include one or more vent holes 46, and the vent hole 46 can be positioned over the waste well 44. The channels 26 include the reagent channel 28, the optical channel 34, and the waste channel 42. These channels 26 provide fluid communication between the inlet port 18, the inlet well 24, the reagent wells 30, the optical wells 36, and the waste well 44, so a vent hole 46 in fluid communication with the waste well 44 is also in fluid communication with the other wells 24, 30, 36 and channels 26, 28, 34. Therefore, a vent hole 46 in fluid communication with the waste well 44 allows for trapped gases and vapors to be vented throughout the disc 10, and liquid flow is facilitated because the liquids are not forcing gases into confined areas, which would develop a resisting back pressure.

Although the illustrated embodiment is fabricated from a transparent medium, in other embodiments the disc 10 could be fabricated from a non-transparent medium, with the limitation that the path light takes through the optical well 36 is relatively transparent to the wavelength of light used. Generally, this means the optical well bottom and top surfaces 38, 40 should be relatively transparent to the wavelength of light used. The material has to be transparent enough to the wavelength of light used to allow for enough light to determine the concentration of the compound being tested for. The intensity of the light source can affect the degree of transparency required for the material around the optical well 36.

The disc 10 can include a source indicator 48 received on the body 12, such as a bar code. The source indicator 48 can be received on any body surface, including the disc top or bottom surface 20, 22 or a body outer edge 53. Positioning the source indicator 48 on the disc top surface 22 may provide less resistance to movement and/or abrasion or wear on the source indicator 48 than either the bottom surface 20 or the body outer edge 53. The source indicator can utilize a wide variety of indicators which can be read, including variations in depth, magnetism, color, shape, size, or position of marks. Any variation which can be read and interpreted can be utilized to indicate source, and the source indicator 48 can be used to indicate which type of tests are to be performed with a particular sample device 10.

The disc 10 can also be used for electrochemical testing. An electrochemical probe 47 can be positioned in an optical well 36, a reagent well 30, or even the waste well 44, with sample device contact points 49 connected to the electrochemical probe 47. When the sample contacts the probe 47 received in the well 30, 36, 44, the probe 47 interacts with the sample, and an electrical signal indicates some characteristic of the sample material. A signal is transmitted from the probe 47 to the sample device contact points 49, which can then be measured to calculate the sample characteristic. The electrical signal can be a measurement of voltage potential, resistance, or current, depending on the type of electrochemical probe 47 utilized. For example, voltage potential is measured when a pH probe is used, and resistance is measured when a conductivity probe is used.

The disc 10 can be fabricated from a number of techniques, such as injection molding, etching, or machining, and can be made from a number of materials, such as acrylic, plastic, glass, quartz, photopolymers, or composite materials. Injection molding of the lid 16 and the bottom plate 14 allows rapid, affordable production of the sample device body 12, and can include formation of the source indicator 48. In one embodiment, the disc 10 is approximately five (5) inches in diameter and approximately 3/8 inches thick, but other sizes are possible without departing from the scope of the present invention.

The Analyzer and Testing

Figure 4:
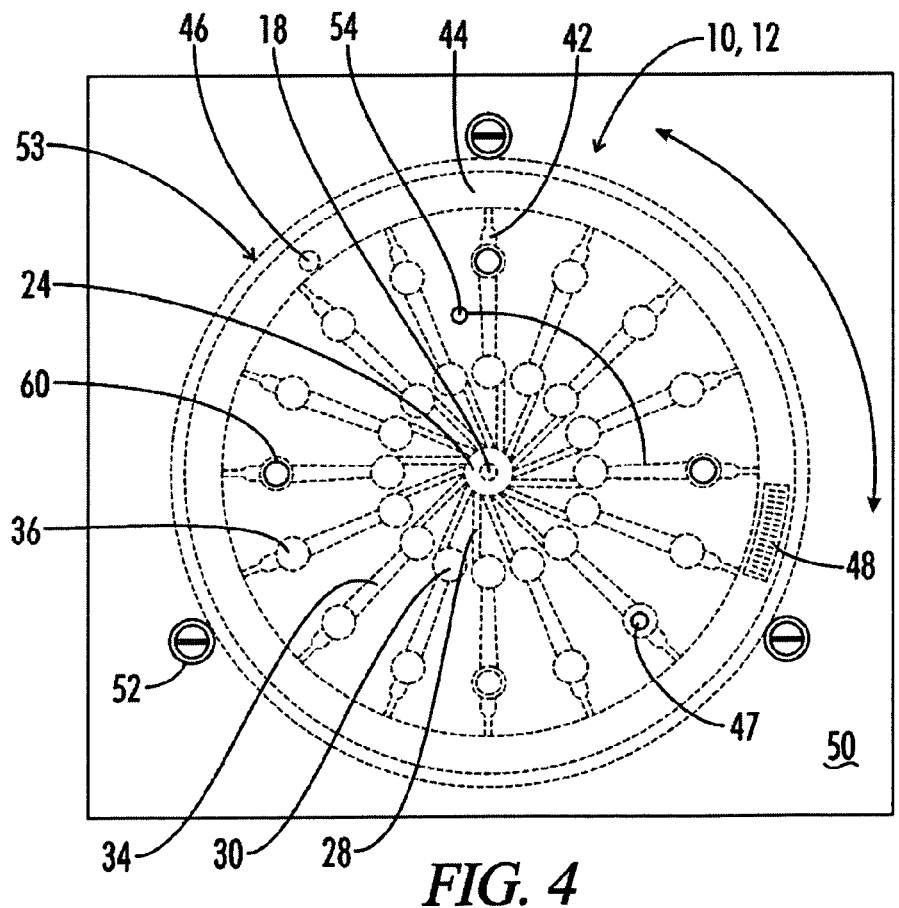
FIG. 4 is a top view of a sample device mounted on the analyzer, with the sample device shown in dotted lines.

A functional representation of one embodiment of the disc 10 mounted on the analyzer 50 is shown in FIGS. 3 and 4. In this embodiment, the disc 10 is mounted on the top of the analyzer 50 between rollers 52. The purpose of the rollers 52 is to constrain and position the disc 10 while permitting it to rotate horizontally. The sample device body outer edge 53 contacts the rollers 52 such that the body outer edge 53 can rotate within the rollers, but the basic position of the outer edge 53 is controlled by the rollers 52. A rotation pin 54 in the analyzer 50 fits into an alignment notch 56 defined in the disc body 12, and can be used to rotate the disc 10 as needed between sample testings so different sub-samples can be sequentially tested. The rotation pin 54 and alignment notch 56 also serve to properly and consistently position and align the disc 10 on the analyzer 50, so the position of each optical well 36 is set and known when an analysis is started. To enable consistent and unique alignment of the disc 10, the alignment notch 56 should be positioned somewhere other than the center of the disc 10.

In the operation of the illustrated embodiment, the disc 10 is placed on the analyzer 50 and an opaque cover 58 is positioned over the disc 10 such that the disc 10 is encased before a test is started. The cover 58 is opened to insert or remove a sample device 10, and the cover 58 on the analyzer 50 is closed during the testing to substantially block out ambient light from the sample device 10. In this embodiment, the sample is injected into the inlet port 18 from the disc bottom surface 20 and is directed via sixteen (16) identical and equally-spaced channels 26 to sixteen (16) optical wells 36. Air or another gas can be introduced into the inlet port 18 after the sample, to move the sample through the disc 10 and to maintain pressure on the sample material, thus helping to keep the optical wells 36 full. The air pressure can be maintained with a line using a valve (not shown) connected to the inlet port 18. The sample could be injected through the same valve. If the inlet port 18 is on the disc bottom surface 20, special fittings can be used to seal the inlet port 18 to the analyzer 50.

After the sample is introduced into the optical wells 36, a source 60 of electromagnetic radiation is activated to transmit into the sample in the optical wells 36, and detectors 62 are positioned to measure the amount of electromagnetic radiation emanating from the optical wells 36. This is used to analyze the samples in the optical wells 36. Generally, the detectors 62 are positioned on the opposite side of the optical wells 36 from the source 60. However, for fluorescence testing, the source 60 and the detector 62 do not have to be aligned, so a wide variety of source 60 and detector 62 positions are possible. In this embodiment, LEDs are used as the radiation source 60, and light is the radiation emitted by the LED source 60, but lasers or other sources of electromagnetic radiation could also be used.

Excess sample water drains into the waste well 44 via waste channels 42. Excess air, forced out when the sample is introduced into the disc 10, exits via the vent hole 46 in the lid 16. The detectors 62 are connected to a microprocessor 66, which performs the required calculations and records the test results. The term "microprocessor" includes any device or collection of devices capable of receiving signals and calculating concentrations or other sample characteristics based on the signals received. A greater concentration of the absorbing material in the optical well 36 results in more light from the LED source 60 being absorbed, and less light reaching the detector 62. Therefore, after proper calibration, the amount of light being detected by the detector can be used to determine the concentration of the absorbing material in the optical well 36. The disc 10 should be encased before the testing operation, or ambient light will reach the detector 62 and bias the test results.

The analyzer 50 can also perform electrochemical analysis if properly configured. Analyzer contact points 68 can be provided on the analyzer 50, with the analyzer contact points 68 positioned to contact the sample device contact points 49 when the sample device 10 is properly positioned on the analyzer 50. The probe 47 in the disc 10 then sends an electronic signal to be read by the microprocessor 66 through the sample device contact points 49, which are in electrical communication with the analyzer contact points 68, which are connected to the microprocessor 66. The analyzer and/or sample device contact points 49, 68 can be a printed board or some sort, a contact pin, contact plates, or any means of providing electrical communication when the analyzer and sample device contact points 49, 68 are aligned. The analyzer 50 can provide an electrical signal to the probe 47 to produce the probe signal, if necessary. It is also possible to include "+" and "−" nodes in a well 30, 36, 44 in place of the probe 47, with the analyzer providing charge to the nodes for other tests such as DNA extraction.

The analyzer 50 can also be equipped with a device 70 for reading the source indicator 48. This can be a bar code reading device 70, but other devices can also be used depending on the type of source indicator 48 used. For example, lasers for detecting depth variation or lights and detectors for reading color variations could be used.

The source indicator 48 could indicate which tests to perform, and the disc 10 could be customized for that pre-determined sample testing routine. The analyzer 50 could have a plurality of sample testing routines, such as one for well water supplies, one for river water supplies, and one for waste water treatment. Such things as the number of sub samples generated, the reagents 32 used, the position of the optical wells 36, and probe 47 positions could be customized for each test routine, and the source indicator 48 allows the analyzer 50 to select the proper testing routine.

In one embodiment of the invention, the analyzer 50 provides four (4) equally-spaced LED source's 60 and four (4) equally-spaced detectors 62 which are used to test sixteen (16) analytes in the sixteen (16) optical wells 36. Each LED source 60 can be at a specific wavelength of light, so the reagents and tests would be grouped based on the required wavelength for the test. With this configuration, the analytes in four (4) optical wells 36 may be analyzed simultaneously. After analysis of four analytes, the analyzer 50 rotates the sample device 10 until the four (4) LED sources 60 underlie four different optical wells 36, and the next four analytes are tested. This process is repeated until all sixteen (16) analytes have been tested.

It may be desirable to leave at least one reagent well 30 empty, and use the associated optical well 36 as a blank for a baseline reading. This baseline can then be applied to other samples tested. The rotation is driven in the illustrated embodiment by the rotation pin 54 on the analyzer 50 that engages in the notch 56 in the disc bottom surface 20. The disc 10 is held in position during the rotation by the rollers 52, so the disc 10 rotates about its center axis. The rotation pin 54 allows the sample device 10 to be rotated between at least two analysis stages, which can be different tests or redundant tests, as desired.

Figure 5:
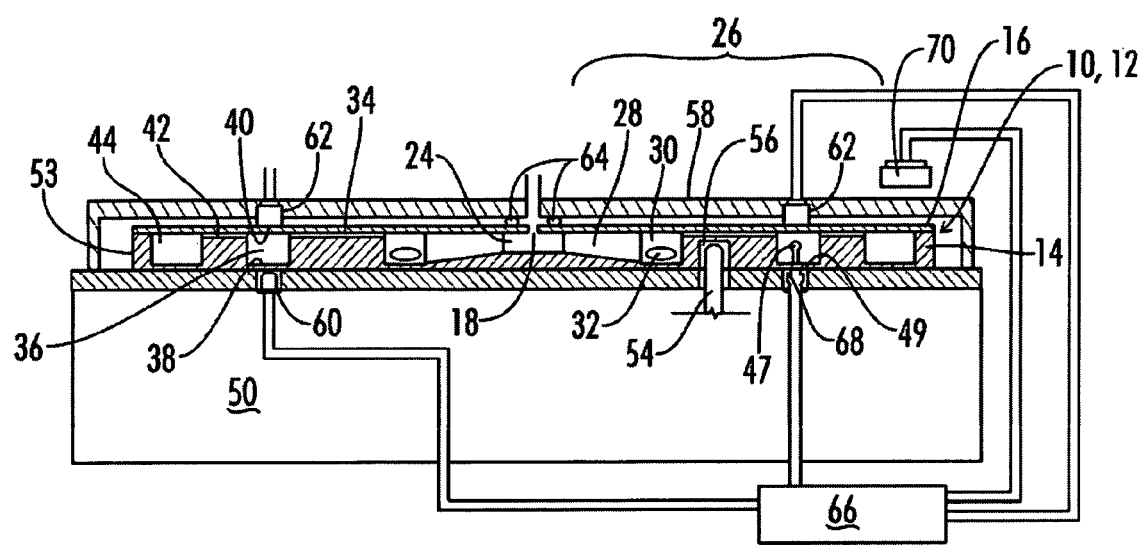
FIG. 5 is a cross-sectional representation of a sample device mounted on an analyzer according to another embodiment of the present invention.

Another embodiment of the present invention is illustrated in FIG. 5. In this embodiment, the inlet port 18 is on the disc top surface 22, and there is no central hole through the disc bottom surface 20. The cover 58 of the analyzer 50 includes a seal 64 that seals against the disc 10 when the cover 58 is closed. Using this embodiment, the sample can be introduced into the disc 10 before the disc 10 is mounted on the analyzer 50, or the sample can be introduced into the disc 10 after the disc 10 is mounted on the analyzer 50 with the cover 58 closed. This seal 64 may be accomplished by any number of methods well known by persons of skill in the art. The seal 64 should block light which can interfere with the optical testing, and the seal may be water-proof to minimize issues associated with leaks.

The disc 10 and analyzer 50 in the illustrated embodiment include sixteen reagent wells 30 and sixteen optical wells 36, and permit four tests to be performed at once. This configuration was chosen in order to permit multiple tests to be performed quickly while keeping the size of the analyzer 50 reasonably small, e.g., smaller than a breadbox. However, other configurations are possible without departing from the scope of the present invention. By way of example only, the analyzer 50 could be enlarged to perform sixteen tests at one time, and thus the rotation of the disc 10 would not be necessary. Further, the size of the disc 10 and the number of optical wells 36 could be varied. Thus, a wide variety of disc 10 and analyzer 50 configurations are possible, depending upon the number and nature of the tests desired to be performed and the size and space limitations of the analyzer 50.

In addition, although the illustrated embodiment of the disc 10 is generally symmetrical, some tests may require a different topography of channels 26 and wells 28, 34, 44. Therefore other configurations and sizes of channels 26 and wells 28, 34, 44 are possible within the scope of the present invention.

While the invention has been described with respect to a limited number of embodiments, those skilled in the art, having the benefit of this disclosure, will appreciate that other embodiments can be devised which do not depart from the scope of the invention as disclosed here. Accordingly, the scope of the invention should be limited only by the attached claims.

We claim:

1. A device for preparing a fluid sample for analysis comprising:
    a body an analyzer coupled to the body and operable to rotate the body;
    an inlet port defined in the body at a center of the body;
    a plurality of reagent wells defined in the body, each reagent well containing at least one reagent, the plurality of reagent wells disposed within the same horizontal plane, the plurality of reagent wells each in fluid communication with the inlet port;
    a plurality of reagent channels defined in the body, wherein the reagent channels extend between the reagent wells and the inlet port such that the sample is divided into a plurality of sub-samples;
    a plurality of optical channels defined in the body, the optical channels all disposed within the same horizontal plane;
    a plurality of optical wells defined in the body, wherein one optical channel connects each optical well to at least one reagent well, and wherein the plurality of optical wells is within the same horizontal plane as the reagent wells, and wherein the optical wells are disposed in the same horizontal plane;
    an alignment notch defined in the body;
    a plurality of waste channels defined in the body; and a waste well defined in the body, wherein the waste well channels extend between the optical wells and the waste wells, wherein the inlet port is connected to a line for receiving pressure from the line through the inlet port to move the sample through the reagent channels to the reagent wells and through the optical channels from the reagent wells to the optical wells.

2. A system comprising a device for preparing a fluid sample for analysis, the device comprising:

a body;

an inlet port defined in the body for introducing the sample;

an inlet well defined in the body and connected to the inlet port, where the inlet well is concentric with the inlet port, and where the inlet well is larger in diameter than the inlet port;

a plurality of reagent wells defined in the body, each reagent well containing at least one reagent;

a plurality of optical wells defined by a body for enabling optical analysis of the sample, wherein the optical wells are in fluid communication with the inlet port and the reagent wells such that the sample is divided into a plurality of sub-samples, and wherein the plurality of optical wells is within the same horizontal plane as the inlet well, the plurality of optical wells configured such that the fluid from the inlet port flows to the optical wells through the reagent wells without rotation of the body, a line connected to the inlet port for providing pressure through the line and the inlet port to move the sample from the inlet well to the reagent wells and the optical wells; and an analyzer operable to rotate the body and to analyze the sample in the optical wells, wherein the inlet port is located at a center of rotation of the body.

3. The system of claim 2 further comprising a plurality of reagent channels defined in the body, wherein the reagent channels provide fluid communication between the inlet port and the reagent wells and sample flow from the inlet port to the reagent wells, and where the reagent channels enter the reagent wells at a tangent of the reagent wells providing agitation for dissolving the reagent.

4. The system of claim 2 wherein the device further comprises:

at least four reagent wells defined in the body, the reagent wells each substantially cylindrical, the reagent wells all disposed within the same horizontal plane;

one reagent channel defined in the body for each reagent well, wherein the reagent channels provide fluid communication between the inlet port and the reagent wells, the reagent channels all disposed within the same horizontal plane; and one optical channel defined in the body for each reagent well, wherein the optical channels provide fluid communication between the reagent wells and the optical wells, the optical channels all disposed within the same horizontal plane.

5. The system of claim 4 wherein the reagent channels radiate from the inlet well.

6. The system of claim 4 wherein the device further comprises:

a waste well defined in the body; and a plurality of waste channels defined in the body, wherein the waste channels provide fluid communication between the waste well and the optical channels.

7. The system of claim 2 wherein the body further comprises a bottom plate and a lid, wherein a seal is formed between the lid and the bottom plate.

8. The system of claim 2 wherein the device further comprises an alignment notch defined in the body at a position other than the center of the body and an outer edge of the body such that the device can be consistently positioned in an analyzer based on the body outer edge and the alignment notch.

9. The system of claim 2 wherein the device further comprises an electrochemical probe and sample device contact point, wherein the electrochemical probe is received in a well selected from the group consisting of the reagent well, the optical well and the waste well, and the sample device contact points are connected to the electrochemical probe.

10. The system of claim 2 wherein the device further comprises a source indicator received on the body.

11. A device for preparing a fluid sample for analysis comprising:

a disk-shaped body comprising a bottom plate affixed to a lid;

an analyzer coupled to the body and operable to rotate the body;

an inlet port defined in the bottom plate for introducing a fluid sample, where the inlet port is positioned in a center of the body, an inlet well defined in the bottom plate and in fluid communication with the inlet port, the inlet well concentric with the inlet port, and the inlet well larger in diameter than the inlet port;

a plurality of radial channels defined in the bottom plate, the radial channels radiating from the inlet well, the radial channels in fluid communication with the inlet well, the radial channels all disposed in a same horizontal plane, the radial channels configured to move fluid from the inlet port to the waste well;

a plurality of reagent wells containing at least one reagent;

a waste well in fluid communication with the radial channels, wherein the inlet port is connected to a line for receiving pressure from the line through the inlet port to move the sample from the inlet port to the reagent wells.

12. The device of claim 11, each radial channel further comprising:

a reagent channel extending linearly between the inlet well and the reagent well;

an optical well; and an optical channel extending between the reagent well and the optical well.

13. The device of claim 11 wherein the body is comprised of a plastic material.

14. The device of claim 11, wherein the waste well extends around the perimeter of the body.

15. The device of claim 11 further comprising an alignment notch defined in the body at a point other than the center of the body.

16. The device of claim 12 where the reagent channels enter the reagent wells at a tangent to the reagent wells.

17. The device of claim 1 where the reagent channels enter the reagent wells at a tangent to the reagent wells.

18. The device of claim 11, wherein the radial channels are equally spaced apart from one another.

19. The device of claim 11, wherein the plurality of radial channels comprises sixteen (16) radial channels.

20. A system for preparing a fluid sample for analysis comprising:

a body comprising: at least one reagent well containing a reagent, at least one optical well, an inlet port, an inlet well for receiving the sample, at least one reagent channel for transferring the sample from the inlet well to the at least one reagent well, and at least one optical channel for transferring the sample from the at least one reagent well to the at least one optical well;

an analyzer coupled to the body and operable to rotate the body; and a line connected to the inlet port for providing pressure through the inlet port to move the sample from the inlet well through the at least one reagent channel to the at least one reagent well and from the at least one reagent well through the at least one optical channel to the at least one optical well, wherein the inlet port is located at a center of rotation of the body.

21. The system of claim 20, wherein the at least one reagent channel enters the at least one reagent well at a tangent of the at least one reagent well such that sample flow from the inlet port to the at least one reagent well provides agitation for dissolving the reagent.

22. The system of claim 20, further comprising an alignment notch defined in the body.

23. The system of claim 20, further comprising a waste well defined in the body.

24. The system of claim 23, further comprising at least one waste channel for transferring the sample from the at least one optical channel to the waste well.

25. The system of claim 20, wherein the inlet well is concentric with the inlet port, and where the inlet well is larger in diameter than the inlet port.

26. The system of claim 25, wherein the inlet well is positioned in the center of the body.

27. The system of claim 25, wherein the inlet well is larger in diameter than the inlet port.

28. The device of claim 1, further comprising a valve connected to the inlet port to maintain pressure through the inlet port.

29. The system of claim 2, wherein the system further comprises a valve connected to the line.

30. The system of claim 2, further comprising an apparatus coupled to the line for providing the pressure.

31. The system of claim 20, further comprising a valve connected to the line.

32. The system of claim 20, wherein the inlet port is positioned at the center axis of the body.

33. The system of claim 20, further comprising an apparatus connected to the line for providing the pressure.

* * * * *